United States Patent
Ye et al.

(10) Patent No.: US 11,834,706 B2
(45) Date of Patent: Dec. 5, 2023

(54) DIGITAL NUCLEIC ACID AMPLIFICATION TESTING METHOD AND INTEGRATED DETECTION SYSTEM BASED ON CRISPR-CAS TECHNOLOGY

(71) Applicant: ZHEJIANG UNIVERSITY, Zhejiang (CN)

(72) Inventors: Zunzhong Ye, Zhejiang (CN); Cui Wu, Zhejiang (CN); Yibin Ying, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 17/924,359

(22) PCT Filed: Oct. 29, 2020

(86) PCT No.: PCT/CN2020/124875
§ 371 (c)(1),
(2) Date: Nov. 10, 2022

(87) PCT Pub. No.: WO2022/036860
PCT Pub. Date: Feb. 24, 2022

(65) Prior Publication Data
US 2023/0175050 A1     Jun. 8, 2023

(30) Foreign Application Priority Data
Aug. 17, 2020   (CN) .......................... 202010824712.0

(51) Int. Cl.
*C12Q 1/6851*   (2018.01)
*B01L 3/00*     (2006.01)
*B01L 7/00*     (2006.01)

(52) U.S. Cl.
CPC ........ *C12Q 1/6851* (2013.01); *B01L 3/50273* (2013.01); *B01L 7/52* (2013.01); *B01L 2200/0642* (2013.01); *B01L 2300/0654* (2013.01); *B01L 2300/0867* (2013.01); *B01L 2300/18* (2013.01)

(58) Field of Classification Search
CPC ..... C12Q 1/6851; B01L 3/50273; B01L 7/52; B01L 2200/0642; B01L 2300/0654; B01L 2300/0867; B01L 2300/18
See application file for complete search history.

(56) References Cited

FOREIGN PATENT DOCUMENTS

| | | |
|---|---|---|
| CN | 104450891 | 3/2015 |
| CN | 105505761 | 4/2016 |
| CN | 105543073 | 5/2016 |
| CN | 108823291 | 11/2018 |
| CN | 110846386 | 2/2020 |
| CN | 111117984 | 5/2020 |
| JP | 2004546689 | * 12/2004 |

OTHER PUBLICATIONS

"International Search Report (Form PCT/ISA/210) of PCT/CN2020/124875," dated Apr. 23, 2021, with English translation thereof, pp. 1-4.
"Written Opinion of the International Searching Authority (Form PCT/ISA/237) of PCT/ CN2020/124875," dated Apr. 23, 2021, pp. 1-4.
Yang, Zhiliu,"Preliminary establishment and Research of Biosensors and Droplet Microfluidic System for Nucleic Acids Detection", Full Text Database of Chinese Excellent Doctoral and Master's Degree Thesis (Master), Engineering Science and Technology I (Monthly), B014-55. Thesis of Master Degree, ZJU, Mar. 2017, pp. 1-95.
Joon Soo Park; et al., "Digital CRISPR/Cas-Assisted Assay for Rapid and Sensitive Detection of SARS-CoV-2," Advanced Science, vol. 8, Issue5, Mar. 3, 2021, 2003564, pp. 1-7.
Hui Wu; et al., "DropCRISPR: A LAMP-Cas12a based digital method for ultrasensitive detection of nucleic acid," Biosensors and Bioelectronics, Sep. 2022, pp. 1-10.

* cited by examiner

*Primary Examiner* — Cynthia B Wilder
(74) *Attorney, Agent, or Firm* — JCIPRNET

(57) ABSTRACT

Disclosed in the present invention are a digital nucleic acid amplification testing method and an integrated detection system based on CRISPR-Cas technology. The integrated detection system comprises an integrated reaction chip, a temperature control module, a light source and an optical signal detector. The method comprises: uniformly dividing a nucleic acid amplification reagent into amplification micro-droplets, then mixing the amplification micro-droplets after digital nucleic acid amplification with detection micro-droplets containing CRISPR-Cas detection reagent to perform a CRISPR reaction, and when the reaction is finished, detecting an optical signal to realize high-specificity testing of a target object, and the concentration or copy number of nucleic acid molecules in a sample to be tested is also obtained, and high-sensitivity absolute quantitative testing of a target object is realized.

4 Claims, 4 Drawing Sheets

DIGITAL NUCLEIC ACID AMPLIFICATION TESTING METHOD AND INTEGRATED DETECTION SYSTEM BASED ON CRISPR-CAS TECHNOLOGY

CROSS-REFERENCE TO RELATED APPLICATION

This application is a 371 of international application of PCT application serial no. PCT/CN2020/124875, filed on Oct. 29, 2020, which claims the priority benefit of China application no. 202010824712.0, filed on Aug. 17, 2020. The entirety of each of the above mentioned patent applications is hereby incorporated by reference herein and made a part of this specification.

FIELD OF THE DISCLOSURE

The disclosure relates to the technical field of microfluidics for nucleic acid testing, in particular to a digital nucleic acid amplification testing method and integrated detection system based on CRISPR-Cas technology.

DESCRIPTION OF RELATED ART

Since Vogelstein et al. published the digital polymerase chain reaction (dPCR) in 1999, dPCR has been found with great technical advantages and application prospects in the fields of food safety, forensic identification, and precision medicine. dPCR is an absolute quantification technology of nucleic acid molecules. By dispersing a sample into tens to tens of thousands of copies to different reaction units, the number of nucleic acid templates in each unit is less than or equal to 1. PCR amplification was performed separately in each unit, after the amplification is finished, the reaction unit with nucleic acid template emits a fluorescent signal, and the reaction unit without template does not have a fluorescent signal, so the number of nucleic acid molecules can be obtained by performing statistical analysis of the fluorescent signal of each reaction unit. When it comes to conventional PCR and real-time fluorescent PCR, the quantitative testing requires DNA with known copy number to formulate a standard curve. However, since the sample measurement conditions are not completely consistent, differences in PCR amplification efficiency will affect the accuracy of quantitative results. According to the principle of dPCR, such technology is not affected by the standard curve and amplification kinetics, and is able to achieve absolute quantification with high sensitivity, high precision, and high tolerance.

Since PCR amplification technology requires precise control of multiple reaction temperatures, practitioners of the art have also developed digital constant temperature nucleic acid technology based on isothermal amplification technology, such as digital loop-mediated isothermal amplification (dLAMP), digital recombinase polymerase amplification (dRPA), and digital multiple displacement amplification (dMDA), etc.

Whether it is dPCR or digital constant temperature amplification technology, the current testing of negative and positive reaction units is mostly based on fluorescence analysis methods, which is performed by adding corresponding fluorescent substances to the sample. The fluorescent substances in the fluorescence analysis method based on nucleic acid amplification mainly include fluorescent dyes and fluorescent probes: (1) fluorescent dyes such as SYBR® series dyes, EvaGreen®, FAM®, etc.; (2) fluorescent probes such as Taqman® probes. However, the fluorescent dyes do not have specificity and cannot distinguish the products of specific amplification and non-specific amplification.

CRISPR (Clustered regularly interspaced short palindromic repeats) is a continuously evolving immune defense mechanism in most bacteria and archaea. CRISPR-associated protein (Cas) work together to form a CRISPR-Cas system with nucleic acid cleavage ability. Based on the above, CRISPR-Cas system can be used as a nucleic acid testing tool. For example, the CRISPR-Cas12a system may identify and capture the target strand according to the designed gRNA (guide Ribonucleic Acid), and its DNA (Deoxyribonucleic Acid) enzyme cleavage activity is activated, thereby efficiently cleaving the single-stranded fluorescent probe in the system, so as to achieve specificity testing of target DNA.

At present, although CRISPR-Cas has been applied in nucleic acid testing, it has not been used in conjunction with digital nucleic acid amplification. On the one hand, detection systems based on digital nucleic acid amplification technology often require multiple instruments such as droplet generators, nucleic acid amplification instruments, and droplet signal detectors, which are poorly integrated, and the operation steps are relatively cumbersome, and therefore improvement still needs to be made in this regard. On the other hand, the operation temperature of nucleic acid amplification technology (for example, PCR technology needs to be denatured into a single strand at a high temperature of 95° C.) is much higher than the tolerance temperature of the reagents in the CRISPR-Cas system (generally 37° C.). Opening the cap and adding the CRISPR-Cas detection reagent after the amplification will cause aerosol contamination, which is likely to cause false positives in subsequent testing results.

Therefore, there is a need to find a method that can solve the above problems. By using digital nucleic acid amplification technology and CRISPR-Cas system together, and their advantages of absolute quantification, high sensitivity and high specificity are combined to develop an integrated detection system, so which may be better utilized in the field of nucleic acid testing.

SUMMARY OF THE DISCLOSURE

The purpose of the present disclosure is to provide a digital nucleic acid amplification testing method and an integrated detection system based on CRISPR-Cas technology in order to solve the problems of conventional technology such as poor integration of the digital detection system and aerosol contamination easily caused due to the use of CRISPR-Cas system. This method combines CRISPR-Cas technology with digital nucleic acid amplification technology to achieve absolute quantitative and high-specificity testing of target nucleic acid molecules. The method of the disclosure simplifies the operation steps while avoiding the contamination of amplification products, and realizes an integrated detection system based on digital nucleic acid amplification and CRISPR-Cas technology.

To achieve the above purpose, the technical scheme adopted in the present disclosure mainly includes:

1. An Integrated Detection System Based on Droplet Digital Nucleic Acid Amplification and CRISPR-Cas:

The system includes an integrated reaction chip, a temperature control module, a light source and an optical signal detector. The integrated reaction chip is distributed with a droplet generating area for amplification reagents, a nucleic acid amplification area, a droplet generating area for detection reagents, a droplet fusion area and an optical detection area. There are microchannels used for connecting the droplet generating area for amplification reagents and the nucleic acid amplification area, connecting the nucleic acid amplification area and the droplet fusion area, connecting the droplet generating area for detection reagents and the droplet fusion area, and connecting the droplet fusion area and the optical detection area.

The light source and the optical signal detector are respectively located on the upper and lower sides of the optical detection area, and the temperature control module is placed below or above the nucleic acid amplification area to heat the nucleic acid amplification area.

The integrated reaction chip is provided with a quick connection structure, and the temperature control module is connected to the nucleic acid amplification area on the integrated reaction chip through the quick connection structure.

A cooling device is placed in the droplet generating area for detection reagents, or a cooling channel is arranged around the droplet generating area for detection reagents, and a coolant is added to the cooling channel.

The width of the microchannel is the same as the size of a single droplet or slightly smaller than the diameter of the droplet, so that only a single droplet can pass through the microchannel in sequence.

2. A Digital Nucleic Acid Amplification Testing Method Based on CRISPR-Cas System:

The solution of the nucleic acid amplification reagent is uniformly divided into tens of thousands of amplification microdroplets, and then the operating environment is selected to realize nucleic acid amplification in the amplification microdroplets. In the meantime, the solution of the CRISPR-Cas detection reagent is uniformly divided into tens of thousands of detection microdroplets. The detection microdroplets and the amplification microdroplets are fused with each other one by one. Thereafter, the CRISPR reaction is performed, and then the high-specificity testing of the target object is realized by detecting the optical signal.

The solution of the nucleic acid amplification reagent enters and passes through the droplet generating area for amplification reagents, and is uniformly divided into tens of thousands of amplification microdroplets, and the nucleic acid amplification area is heated by the temperature control module. Thereafter, the amplification microdroplets are driven to pass through the microchannel and enter the nucleic acid amplification area at a fixed flow rate to realize digital nucleic acid amplification.

The droplet generating area for amplification reagents controls the generation of droplets by adjusting the structure and the two-phase flow rate ratio through the micro-pipe structure based on T-channel method, flow focusing method or coaxial flow focusing method. Two-phase refers to a two-phase liquid of a solution/droplet and its surrounding oil.

The diameters of the amplification microdroplets range from nanometers to micrometers, and the number thereof may range from tens of thousands to millions, but the diameters of the droplets produced each time are almost the same, and the size of the droplets prepared each time is uniform.

The amplification technique may be polymerase chain reaction (PCR), loop-mediated isothermal amplification (LAMP), nucleic acid sequence-dependent amplification (NASBA), rolling circle amplification (RCA), helicase-dependent amplification technology (HDA), recombinase polymerase amplification (RPA), multiple strand displacement amplification (MDA), etc.

The solution of the CRISPR-Cas detection reagent is uniformly divided into tens of thousands of testing droplets in the droplet generating area for detection reagents, and the detection droplets contain a single-stranded oligonucleotides probe labeled with fluorescence groups as a fluorescent probe.

The droplet generating area for detection reagents controls the generation of droplets by adjusting the structure and the two-phase flow rate ratio through the micro-pipe structure based on T-channel method, flow focusing method or coaxial flow focusing method and so on.

The diameters of the detection microdroplets range from nanometers to micrometers, and the number thereof may range from tens of thousands to millions, but the diameters of the droplets produced each time are almost the same, and the size of the droplets prepared each time is uniform.

The amplification microdroplets after undergoing amplification in the nucleic acid amplification area enter the droplet fusion area along with the detection microdroplets at a fixed flow rate. The collision and aggregation of droplets are performed to carry out fusion of one amplification microdroplet and one detection microdroplet respectively to form mixed microdroplets, and then the mixed microdroplets are subjected to CRISPR reaction.

After the CRISPR reaction is completed, the mixed microdroplets enter the optical detection area, and the target strand in the mixed microdroplets is identified and captured through gRNA, and the DNA enzyme cleavage activity thereof is activated.

If the mixed microdroplet contains a target strand, the fluorescent probe is cleaved, so that the fluorescence group and the quencher group are separated, and a fluorescent signal is emitted under the excitation of the light source. The fluorescent signal of a single mixed microdroplet is analyzed through an optical signal detector to obtain a ratio of negative droplets (without fluorescent signals) and the ratio of the positive droplets (with fluorescent signals). Then, the concentration or copy number of nucleic acid molecules is calculated, so as to obtain an absolute quantitative testing result.

The droplet fusion area is a Y-shaped or T-shaped microchannel, and the three ends of the Y-shaped or T-shaped microchannel are respectively connected with the nucleic acid amplification area, the droplet generating area for detection reagents and the optical detection area through the respective microchannels.

The droplets in the microchannel are driven by the oil phase flowing around them, and the flow rate of the oil phase is controlled through a pump.

One of the following two different methods is adopted as the method of obtaining the ratio of negative droplets and the ratio of the positive droplets:

(A) Mixed microdroplets are detected one by one:

The mixed microdroplets are driven to flow through the optical detection area in sequence. Under the excitation of the light source or without the excitation of the light source (if there are no fluorescent materials in the mixed microdroplet, the light source for excitation is not required), the optical signal detector, such as photomultiplier tube and photodetector, detects the optical signal and converts the optical signal into an electric signal. The optical signal of the mixed microdroplet is continuously recorded, and a ratio p of positive droplets is obtained by filtering the waveform of the electrical signal, removing the baseline, and segmenting the threshold value.

A negative droplet refers to a mixed microdroplet with no fluorescent signal, that is, the droplet does not contain nucleic acid molecules; a positive droplet refers to a mixed microdroplet with a fluorescent signal, that is, the droplet contains at least one nucleic acid molecule.

(B) All mixed microdroplets are detected simultaneously: All mixed microdroplets converge in the optical detection area and are arranged dispersedly. Under the excitation of a light source or without the excitation of a light source (if there are no fluorescent materials in the mixed microdroplet, the light source for excitation is not required), the optical inspection area is photographed using a camera or a mobile phone with a photo function to obtain an optical image, and the ratio p of positive droplets is obtained through image processing, including acquisition of regions of interest, filtering, threshold segmenting, and counting.

The method finally calculates the average number of nucleic acid molecules $\lambda$ in each mixed microdroplet according to the ratio p of positive droplets according to the following formula, so as to obtain the concentration or copy number of nucleic acid molecules in the sample to be tested:

$$\lambda = -\ln(1-p).$$

The advantageous effects of the present disclosure are as follows:

1. The present disclosure realizes the combination of digital nucleic acid amplification technology and CRISPR-Cas system for application in the field of nucleic acid testing for the first time, which not only has the features of absolute quantification and high tolerance of digital amplification technology but also has the advantages of high-sensitivity and high-specificity of CRISPR-Cas system.

2. The integrated detection system based on droplet digital nucleic acid amplification and CRISPR-Cas system provided in the present disclosure, integrates droplet generation, nucleic acid amplification, and fluorescence detection on a single chip, so that the operation steps are simplified, and the cross-contamination is avoided by the opening the cap and adding the detection reagents after nucleic acid amplification.

3. The present disclosure only regulates the temperature of the nucleic acid amplification area, and cooling equipment or coolant may be added in the droplet generating area for detection reagents, which overcomes the influence of high temperature on the activity of reagents in the CRISPR-Cas system and ensures the accuracy of testing.

4. The temperature control module used in the present disclosure can be disassembled, and a temperature-variable control module or a constant temperature control module may be selected according to the amplification technology adopted. The optical detection method may also be selected from two methods, namely detecting mixed microdroplets one by one and detecting all mixed microdroplets simultaneously, thereby improving the usability of the system.

5. The present disclosure has a simple structure, small size, high portability, and is suitable for use in the field.

Figure 1:
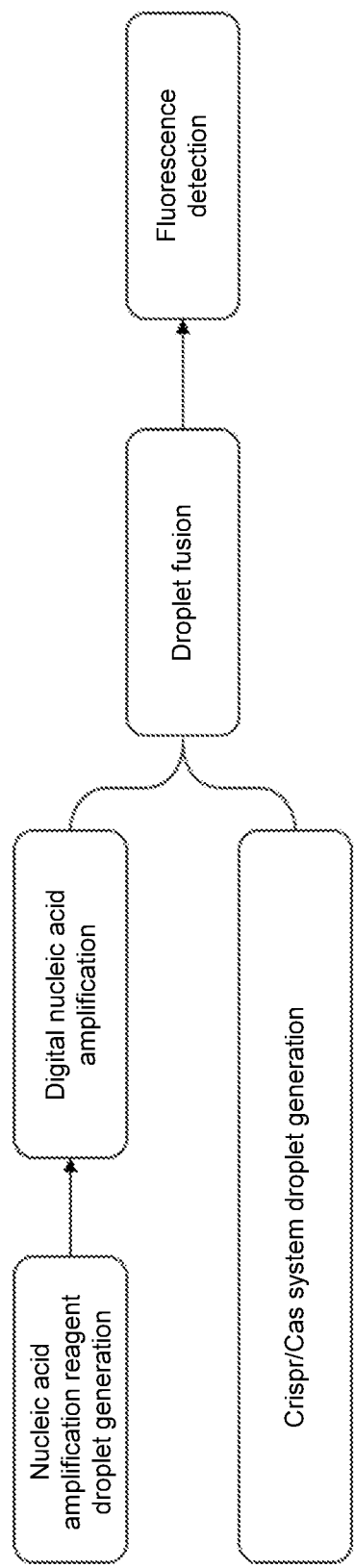
FIG. 1 is a testing flow chart of the present disclosure.

In the figure: nucleic acid amplification reagent 1, CRISPR-Cas detection reagent 2, integrated reaction chip 3, droplet generating area for amplification reagents 4, microchannel 5, nucleic acid amplification area 6, droplet generating area for detection reagents 7, droplet fusion area 8, optical detection area 9, quick connection structure 10, cooling channel 11, amplification microdroplet 12, detection microdroplet 13, mixed microdroplet 14.

DESCRIPTION OF EMBODIMENTS

The present disclosure will be further described below with reference to the accompanying drawings, but the present disclosure is not limited to the following embodiments.

Figure 2:
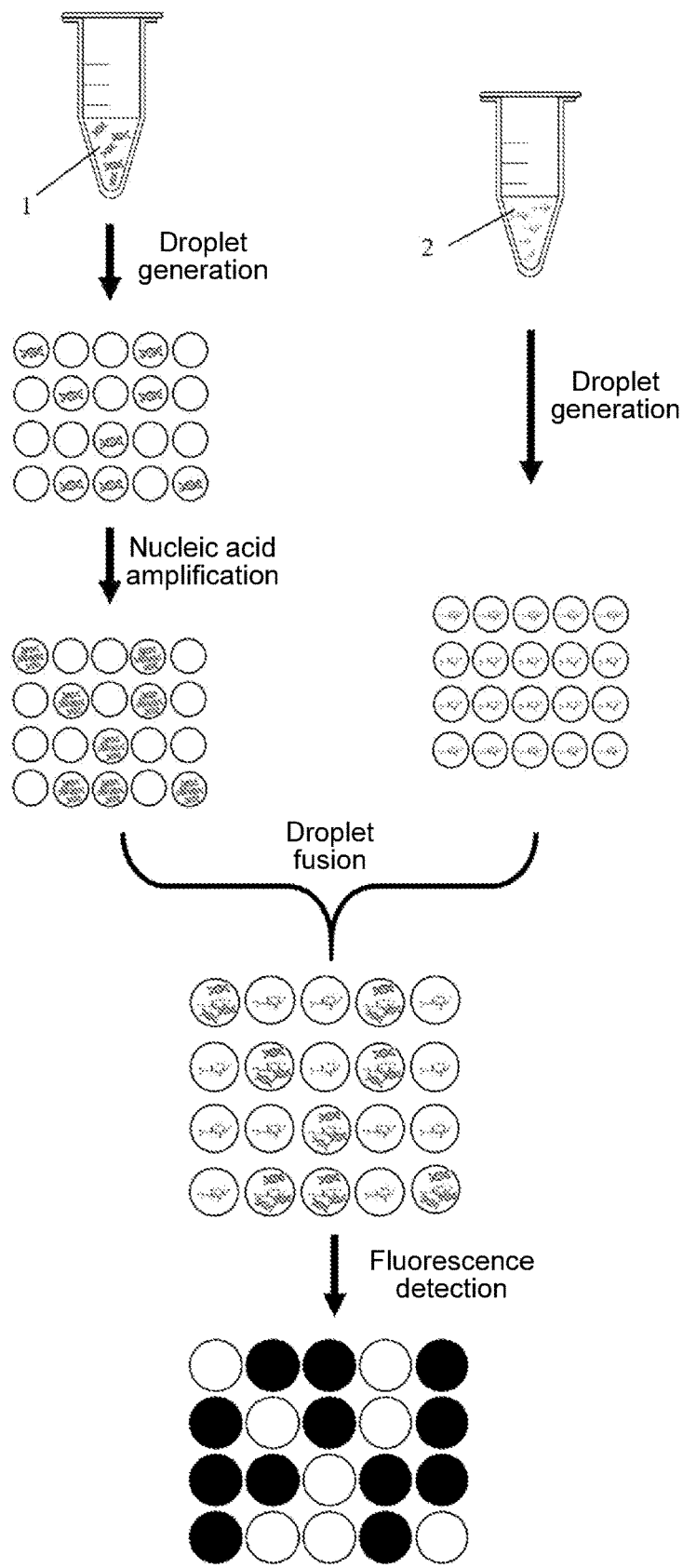
FIG. 2 is a testing principle diagram of the present disclosure.
Figure 3:
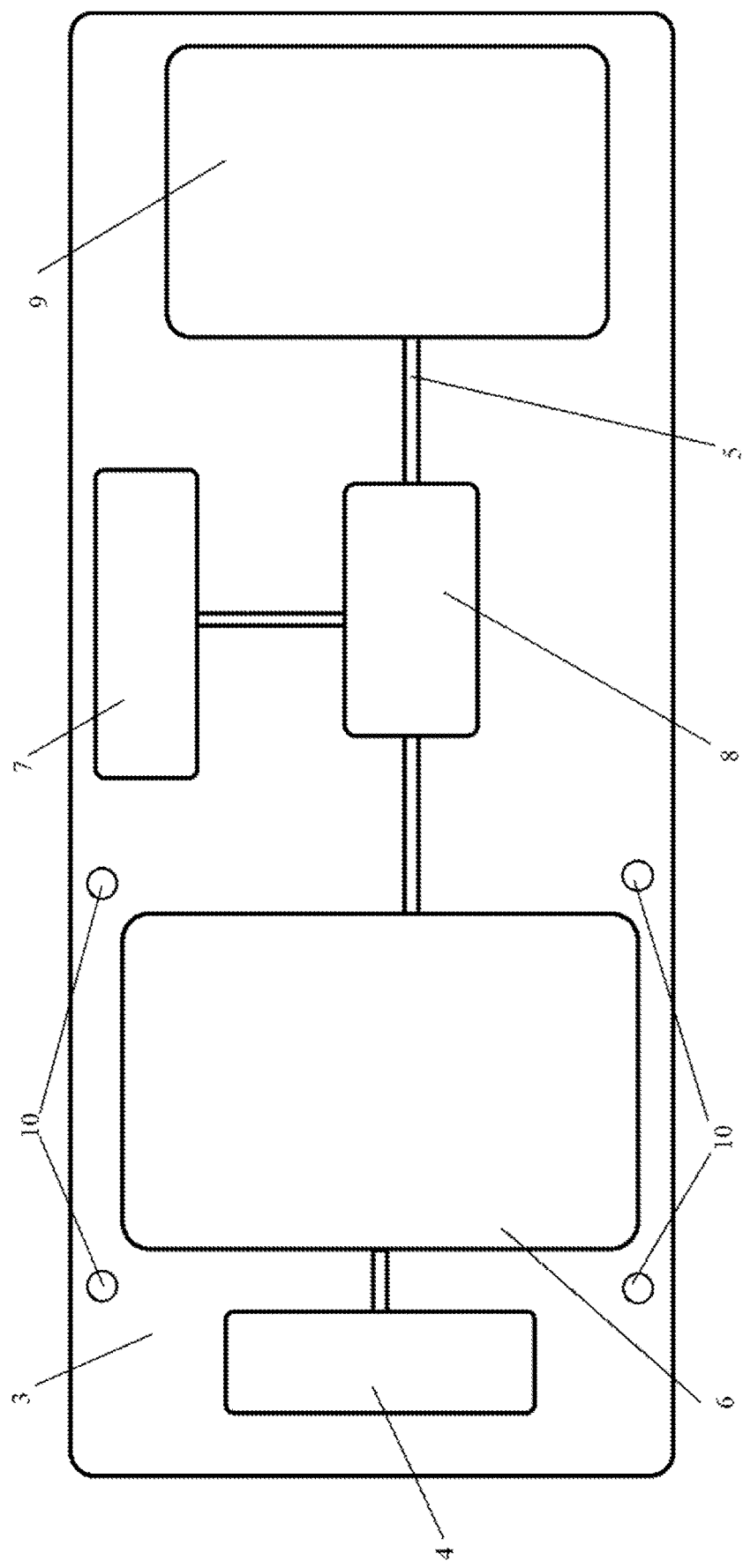
FIG. 3 is a top view of an integrated reaction chip in the present disclosure.

Specifically, the detection process of embodiment is shown in FIG. 1 and FIG. 2. The embodiment includes an integrated reaction chip 3, a temperature control module, a light source and an optical signal detector. As shown in FIG. 3, the integrated reaction chip 3 is distributed with a droplet generating area for amplification reagents 5, a nucleic acid amplification area 6, a droplet generating area for detection reagents 7, a droplet fusion area 8 and an optical detection area 9. There are microchannels 5 used for connecting the droplet generating area for amplification reagents 4 and the nucleic acid amplification area 6, connecting the nucleic acid amplification area 6 and the droplet fusion area 8, connecting the droplet generating area for detection reagents 7 and the droplet fusion area 8, and connecting the droplet fusion area 8 and the optical detection area 9.

The light source and the optical signal detector are respectively located on the upper and lower sides of the optical detection area 9, and the temperature control module is placed above or below the nucleic acid amplification area 6 to heat the nucleic acid amplification area 6. When the digital nucleic acid amplification is finished, the temperature control module may be turned off or removed.

The temperature control module is suitable for a variable temperature environment of PCR, and may also realize the constant temperature environment suitable for constant temperature amplification technologies such as LAMP, RPA, and NASBA.

The integrated reaction chip 3 is provided with a quick connection structure 10, and the temperature control module is connected to the nucleic acid amplification area 6 on the integrated reaction chip 3 through the quick connection structure 10, so that the temperature control module and the nucleic acid amplification area 6 are positioned and fixed through the quick connection structure 10. In a specific implementation, the quick connection structure 10 can be a connection structure based on magnet attraction, a snap structure based on simple rotation, a snap structure based on push-type self-locking, etc.

Figure 4:
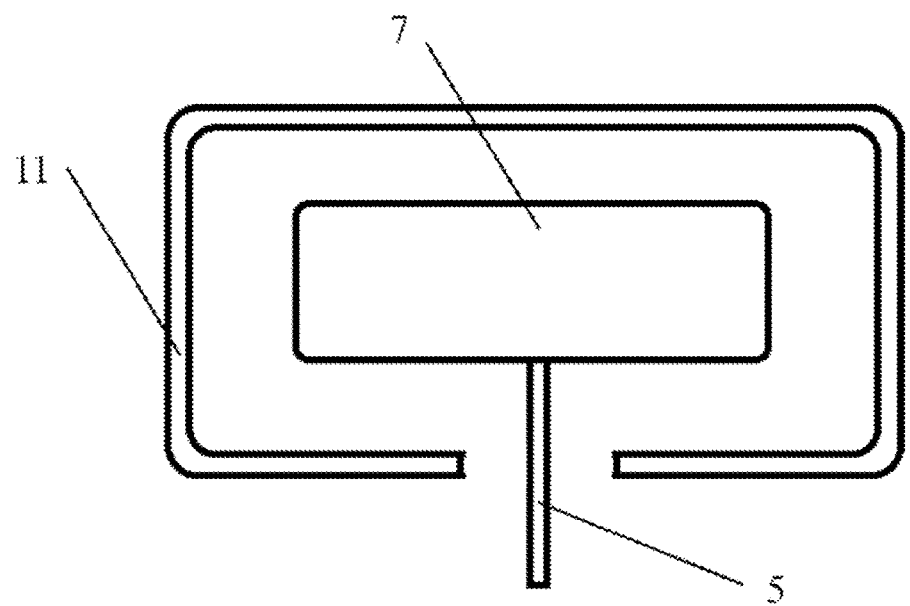
FIG. 4 is a top view of a cooling channel in the integrated reaction chip of the present disclosure.

A cooling device is placed in the droplet generating area for detection reagents 7 in the amplification process, or a cooling channel 11 is arranged around the droplet generating area for detection reagents 7. As shown in FIG. 4, a coolant is added to the cooling channel 11, so that the droplet generating area for detection reagents 7 is cooled during the amplification process.

The width of the microchannel 5 is the same as the size of a single droplet, so that only a single droplet can pass through the microchannel 5 in sequence.

The light source may be a light emitting diode LED, a laser diode, or the like.

The optical signal detector may be a photomultiplier, a PMT, a photodiode, a CCD (Charge Coupled Device), a mobile phone with a camera function, an optical microscope, and the like.

The cooling device may be a cool fan, a heat sink, coolant, and so on for cooling temperature.

Figure 5:
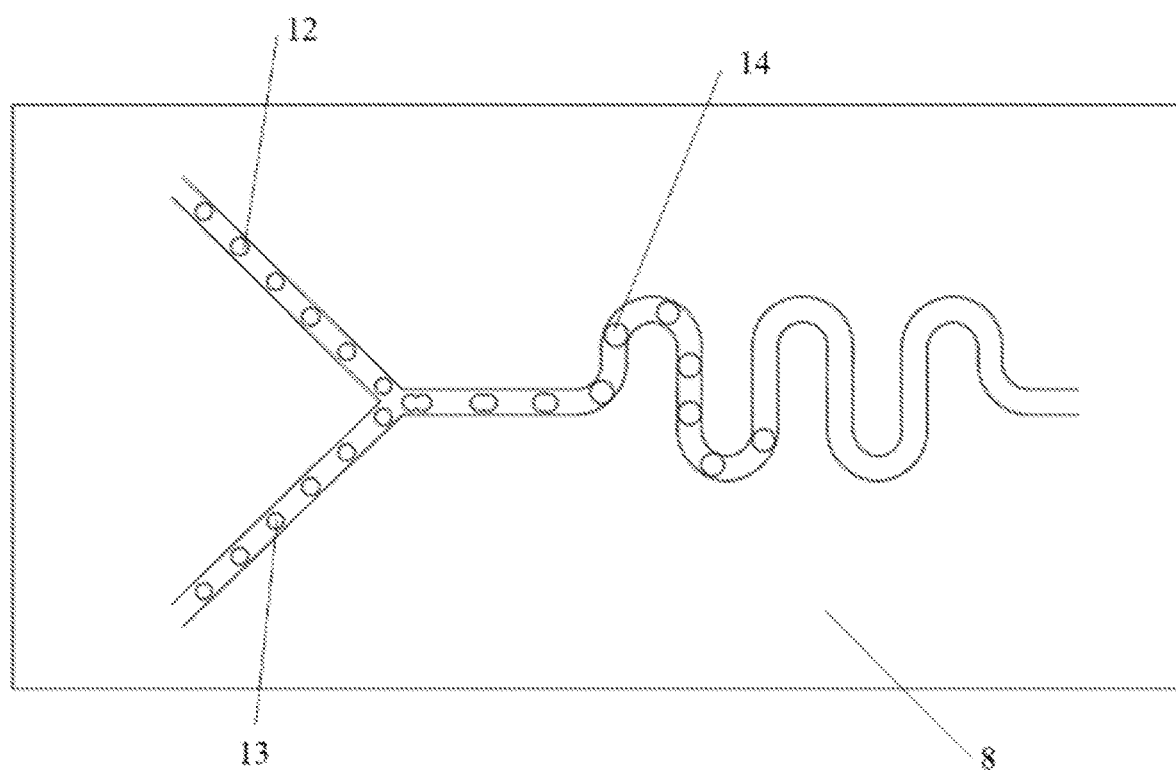
FIG. 5 is a top view of a droplet fusion area (Y-shaped microchannel) in the integrated reaction chip of the present disclosure.

As shown in FIG. 5, the droplet fusion area 8 is a Y-shaped microchannel, and the three ends of the Y-shaped microchannel are respectively connected with the nucleic acid amplification area 6, the droplet generating area for detection reagents 7 and the optical detection area 9 through the respective microchannels 5.

The droplet generating area for amplification reagents 4 and the droplet generating area for detection reagents 7 are both droplet generating areas, and they can control the generation and size of droplets by adjusting the structure and the two-phase flow rate ratio through the micro-pipe structure based on T-channel method, flow focusing method or coaxial flow focusing method.

The nucleic acid amplification area 6 and the temperature control module are positioned and fixed through a quick connection structure, for example, a connection structure based on magnet attraction. The temperature control module may be selected according to the amplification technology adopted. If the polymerase chain reaction (PCR) is adopted, the temperature control module may be selected from the variable temperature control module or the multi-temperature zone control module; if the constant temperature amplification technology such as LAMP is adopted, the temperature control module may be selected from a single temperature zone control module.

In order to prevent the temperature of the nucleic acid amplification area 6 from affecting the activity of the reagents in the CRISPR-Cas system, the temperature control module only regulates the temperature of the nucleic acid amplification area on the integrated reaction chip 3. When the digital nucleic acid amplification is finished, the temperature control module may be turned off or removed.

When amplification is completed, the amplified microdroplet 12 and the detection microdroplet 13 enter the droplet fusion area 8 at a fixed flow rate. Through the appropriate flow channel design, the two microdroplets are brought into contact and fused together, and then subjected to the CRISPR reaction. The detection of target objects is realized by detecting the optical signals. For example, the CRISPR-Cas detection reagent includes a single-stranded oligonucleotide probe labeled with fluorescence groups. After the CRISPR reaction is completed, the target strand can be identified and captured through gRNA, and the DNA enzyme cleavage activity thereof is activated. If the mixed microdroplet 14 contains a target strand, the fluorescent probe is cleaved, so that the fluorescence group and the quencher fluorescence group are separated, and a fluorescent signal is emitted when excited by a light source of a certain wavelength.

To perform optical signal detection, two different methods may be adopted for implementation:

(1) Mixed microdroplets 14 are detected one by one: In this method, the mixed microdroplets 14 flow through the optical detection area one by one in sequence at a fixed rate. Under the excitation of the light source with a certain wavelength (if there are no fluorescent materials in the mixed microdroplet, the light source for excitation is not required), the optical signal detector, such as PMT and photodetector, converts the optical signal into an electric signal. The optical signal of the mixed microdroplet 14 is continuously recorded, and a ratio of positive droplets can be obtained by filtering the waveform of the electrical signal, removing the baseline, and segmenting the threshold value.

(2) All mixed microdroplets are detected simultaneously: In this method, all mixed microdroplets 14 converge in the optical detection area. Under the excitation of the light source with a certain wavelength (if there are no fluorescent materials in the mixed microdroplet, the light source for excitation is not required), the optical inspection area is photographed using a camera or a mobile phone with a photo function to obtain an optical image, and the ratio of positive droplets can be obtained through image processing, including acquisition of regions of interest, filtering, threshold segmenting, and counting.

No matter in the method (1) or the method (2), the proportion p of positive droplets may be obtained. According to the Poisson distribution principle, the average number of nucleic acid molecules $\lambda$ in each mixed microdroplet 14 may be calculated according to the following formula, so as to obtain the concentration or copy number of nucleic acid molecules in a sample to be tested.

$$\lambda = -\ln(1-p).$$

Below is a combination of the method of the present disclosure and the integrated detection system, the content of the present disclosure and the implementation process are further elaborated:

1) Preparation of liquid to be tested:

① The required nucleic acid amplification reagent 1 is prepared according to the actual amplification technology adopted.

② A CRISPR-Cas detection reagent 2 with suitable concentration is prepared.

2) The prepared nucleic acid amplification reagent 1 is added to the droplet generating area for amplification reagents 4 of the integrated reaction chip 3 to generate the amplification microdroplet 12 required for digital nucleic acid amplification.

3) A suitable temperature control module is selected according to the adopted amplification technology, the nucleic acid amplification area 6 on the integrated reaction chip 3 is fixed above the temperature control module through the quick connection structure 10, and the power of the temperature control module is turned on for heating, thus achieving nucleic acid amplification.

4) The prepared CRISPR-Cas detection reagent 2 is added to the droplet generating area for detection reagents 7 of the integrated reaction chip 3 to generate the detection microdroplet 13 required for optical detection. In order to reduce the influence of the amplification heating process on the activity of the reagents in the CRISPR-Cas detection reagent 2, a coolant may be added in the cooling channel 11.

5) After the digital nucleic acid amplification is performed, the temperature control module is turned off, the amplification microdroplet 12 and the detection microdroplet 13 flow into the droplet fusion area 8 at a certain flow rate, as shown in FIG. 5. After passing through the Y-shaped microchannel, the two droplets are fused one by one, followed by a CRISPR reaction in the mixed microdroplet 14.

6) When the CRISPR reaction is completed, the optical signal of a single mixed microdroplet 14 can be obtained. There are two methods to implement the process:

① Mixed microdroplets 14 are detected one by one: In this method, the mixed microdroplets 14 flow through the optical detection area one by one in sequence at a fixed rate. Under the excitation of the light source with a certain wavelength, a PMT or a photodetector can be used to convert the optical signal into an electric signal. The optical signal of the mixed microdroplet 14 is recorded.

② All microdroplets are detected simultaneously: In this method, all mixed microdroplets 14 converge in the optical detection area. Under the excitation of the light source with a certain wavelength, a camera or a mobile phone with a photographing function is utilized to take pictures of the optical detection area to obtain an optical image.

7) The two optical signal acquisition methods described in step 6) respectively correspond to two different optical signal processing and result analysis methods:

① After obtaining the optical signal of each droplet in the mixed microdroplet 14, a ratio p of positive droplets can be obtained by filtering the waveform of the electrical signal, removing the baseline, and segmenting the threshold value.

② After obtaining the optical image of the mixed microdroplet 14, the ratio p of positive droplets can be obtained through image processing for acquisition of regions of interest, filtering, threshold segmenting, and counting.

According to method ① or method ②, the proportion of positive droplets can be obtained, and the concentration or copy number of nucleic acid molecules in the sample to be tested can be calculated according to the Poisson distribution principle, and the detection result can be obtained.

8) The integrated reaction chip 3 is removed and replaced with a new integrated reaction chip or the detection is terminated.

The above-mentioned specific embodiments are used to explain the present disclosure, rather than limit the present disclosure. Within the spirit of the present disclosure and the scope to be protected by the claims, any modifications and revisions made to the present disclosure all fall into the scope to be protected by the present disclosure.

What is claimed is:

1. An integrated detection system based on droplet digital nucleic acid amplification and CRISPR-Cas technology, comprising an integrated reaction chip, a temperature control module, a light source and an optical signal detector; wherein the integrated reaction chip is distributed with a droplet generating area for amplification reagents, a nucleic acid amplification area, a droplet generating area for detection reagents, a droplet fusion area and an optical detection area; there are microchannels used for connecting the droplet generating area for amplification reagents and the nucleic acid amplification area, connecting the nucleic acid amplification area and the droplet fusion area, connecting the droplet generating area for detection reagents and the droplet fusion area, and connecting the droplet fusion area and the optical detection area; the light source and the optical signal detector are respectively located on upper and lower sides of the optical detection area, and the temperature control module is placed below or above the nucleic acid amplification area to heat the nucleic acid amplification area, the droplet fusion area is a Y-shaped or T-shaped microchannel, and three ends of the Y-shaped or T-shaped microchannel are respectively connected with the nucleic acid amplification area, the droplet generating area for detection reagents and the optical detection area through respective microchannels;

a width of the microchannel is the same as a size of a single droplet or slightly smaller than the diameter of the droplet, so that only the one single droplet passes through the microchannel in sequence;

the nucleic acid amplification area contains a solution of nucleic acid amplification reagent, which is generated into amplification microdroplets;

the droplet generating area for detection reagents contains the solution of CRISPR-Cas detection reagent, and the solution of CRISPR-Cas detection reagent is generated into detection microdroplets;

the amplification microdroplets after undergoing amplification in the nucleic acid amplification area enter the droplet fusion area along with the detection microdroplets at a fixed flow rate, collision and aggregation of droplets are performed to carry out fusion of one of the amplification microdroplets and one of the detection microdroplets respectively to form mixed microdroplets, and the mixed microdroplets are subjected to the CRISPR reaction, wherein a cooling device is placed in the testing system droplet generating area, or a cooling channel is arranged around the droplet generating area for detection reagents, and a coolant is added to the cooling channel.

2. The integrated detection system based on droplet digital nucleic acid amplification and CRISPR-Cas technology according to claim 1, wherein the integrated reaction chip is provided with a connection structure, and the temperature control module is connected to the nucleic acid amplification area on the integrated reaction chip through the connection structure.

3. A digital nucleic acid amplification testing method based on CRISPR-Cas technology applied to the integrated detection system claimed in claim 1, comprising: uniformly dividing a solution of the nucleic acid amplification reagent into tens of thousands of amplification microdroplets; at the same time, uniformly dividing the solution of CRISPR-Cas detection reagents into tens of thousands of detection microdroplets; fusing the detection microdroplets and the amplification microdroplets with each other one by one, afterwards, performing a CRISPR reaction, and realizing a high-specificity testing of a target object by detecting an optical signal;

the solution of the nucleic acid amplification reagent enters and passes through the droplet generating area for amplification reagents, and is uniformly divided into tens of thousands of the amplification microdroplets, and the nucleic acid amplification area is heated by the temperature control module; afterwards, the amplification microdroplets are driven to pass through microchannels and enter the nucleic acid amplification area at a fixed flow rate to achieve digital nucleic acid amplification;

the solution of the CRISPR-Cas detection reagent is uniformly divided into tens of thousands of the detection microdroplets in the droplet generating area for detection reagents, and the detection microdroplets contain a single-stranded oligonucleotides probe labeled with fluorescence groups as a fluorescent probe;

the amplification microdroplets after undergoing amplification in the nucleic acid amplification area enter the droplet fusion area along with the detection microdroplets (13) at the fixed flow rate, collision and aggregation of droplets are performed to carry out fusion of one of the amplification microdroplets and one of the detection microdroplets respectively to form mixed microdroplets, and the mixed microdroplets are subjected to the CRISPR reaction;

when the CRISPR reaction is completed, the mixed microdroplets enter the optical detection area, and a target strand in the mixed microdroplets is identified and captured through gRNA, and a DNA enzyme cleavage activity is activated; if the mixed microdroplet contains the target strand, the fluorescent probe is cleaved, so that the fluorescence group and a quencher group are separated, and a fluorescent signal is emitted under excitation of the light source, the fluorescent signal of the single mixed microdroplet is analyzed through the optical signal detector to obtain a ratio of positive droplets, and then a concentration or a copy number of nucleic acid molecules in the nucleic acid amplification reagent is calculated, so as to obtain a detection result.

4. The digital nucleic acid amplification testing method based on CRISPR-Cas technology according to claim 3, wherein one of the following two methods is adopted to obtain the ratio of positive droplets:

(A) the mixed microdroplets are detected one by one:

the mixed microdroplets are driven to flow through the optical detection area in sequence, the optical signal detector detects an optical signal and converts the optical signal into an electric signal, and a ratio p of the positive droplets is obtained through processing of the electrical signal;

(B) all microdroplets are detected simultaneously: all of the mixed microdroplets converge in the optical detection area and are arranged dispersedly, a camera or a mobile phone with a photographing function is utilized to take pictures of the optical detection area to obtain an optical image, and the ratio p of the positive droplets is obtained through image processing;

the method finally calculates an average number of nucleic acid molecules $\lambda$ in each of the mixed microdroplets according to the ratio p of the positive droplets according to the following formula, so as to obtain a concentration or a copy number of the nucleic acid molecules in a sample to be tested:

$\lambda = -\ln(1-p)$.

* * * * *